(12) United States Patent
Fung et al.

(10) Patent No.: US 6,221,655 B1
(45) Date of Patent: Apr. 24, 2001

(54) SPIN FILTER ASSEMBLY FOR ISOLATION AND ANALYSIS

(75) Inventors: Bernard Kwok-Keung Fung, Irvine; Sohail Jahid, Costa Mesa, both of CA (US)

(73) Assignee: Cytosignal, Irvine, CA (US)

( * ) Notice: Subject to any disclaimer, the term of this patent is extended or adjusted under 35 U.S.C. 154(b) by 0 days.

(21) Appl. No.: 09/127,618

(22) Filed: Aug. 1, 1998

(51) Int. Cl.[7] .................................................. G01N 33/543
(52) U.S. Cl. .................... 435/288.1; 435/7.1; 436/518; 436/538; 436/541; 422/58; 422/61; 422/68.1; 422/72; 422/99; 422/101; 422/104
(58) Field of Search ............................... 422/58, 61, 68.1, 422/72, 99, 101, 104; 435/7.1, 288.1; 436/518, 538, 541

(56) References Cited

U.S. PATENT DOCUMENTS

| | | | |
|---|---|---|---|
| 3,661,265 | * | 5/1972 | Greenspan . |
| 3,870,639 | * | 3/1975 | Moore et al. . |
| 4,136,036 | * | 1/1979 | Columbus . |
| 4,214,993 | * | 7/1980 | Forsythe, Jr. et al. . |
| 4,417,981 | * | 11/1983 | Nugent . |
| 4,436,631 | * | 3/1984 | Graham, Jr. et al. . |
| 4,623,461 | * | 11/1986 | Hossom et al. . |
| 4,683,058 | | 7/1987 | Lyman et al. ......................... 210/359 |
| 4,891,134 | * | 1/1990 | Vcelka . |
| 4,990,253 | * | 2/1991 | Vcelka . |
| 5,104,533 | * | 4/1992 | Szabados . |
| 5,254,314 | * | 10/1993 | Yu et al. . |
| 5,257,984 | * | 11/1993 | Kelley . |
| 5,455,009 | * | 10/1995 | Vogler et al. . |
| 5,456,885 | * | 10/1995 | Coleman et al. . |
| 5,935,858 | * | 8/1999 | Herst . |

OTHER PUBLICATIONS

The Immunocatcher, Cytosignal Products.*
Millipore Direct, 1991.*
Baxter Scientific Products, pp. RD26 and 50, 1991.*

* cited by examiner

Primary Examiner—Christopher L. Chin
Assistant Examiner—Bao-Thuy Nguyen
(74) Attorney, Agent, or Firm—Maria Erlinda Co Sarno

(57) ABSTRACT

This invention relates to a spin filter assembly and its usage to facilitate the isolation and analyses of molecules and compounds such as proteins present in various biological and non-biological solutions. The spin filter assembly of this invention comprise of a tube having an open top end, a bottom end opposite the open top end, a body of a first length, an inner diameter and a first outer diameter, a filter means at the bottom end, the tube insertable to an upper portion of a centrifuge holder having a closed lower end, an open upper end, a length longer than the first length of the tube, and a second inner diameter greater than the first outer diameter of the tube; and, a container closure means that fits on top of the open end of the tube. The spin filter assembly can be a component of a sample preparation or assay kit, for example, a kit for analyzing proteins by immunoprecipitation. A process for analyzing proteins by immunoprecipitation using the spin filter assembly is described.

32 Claims, 3 Drawing Sheets

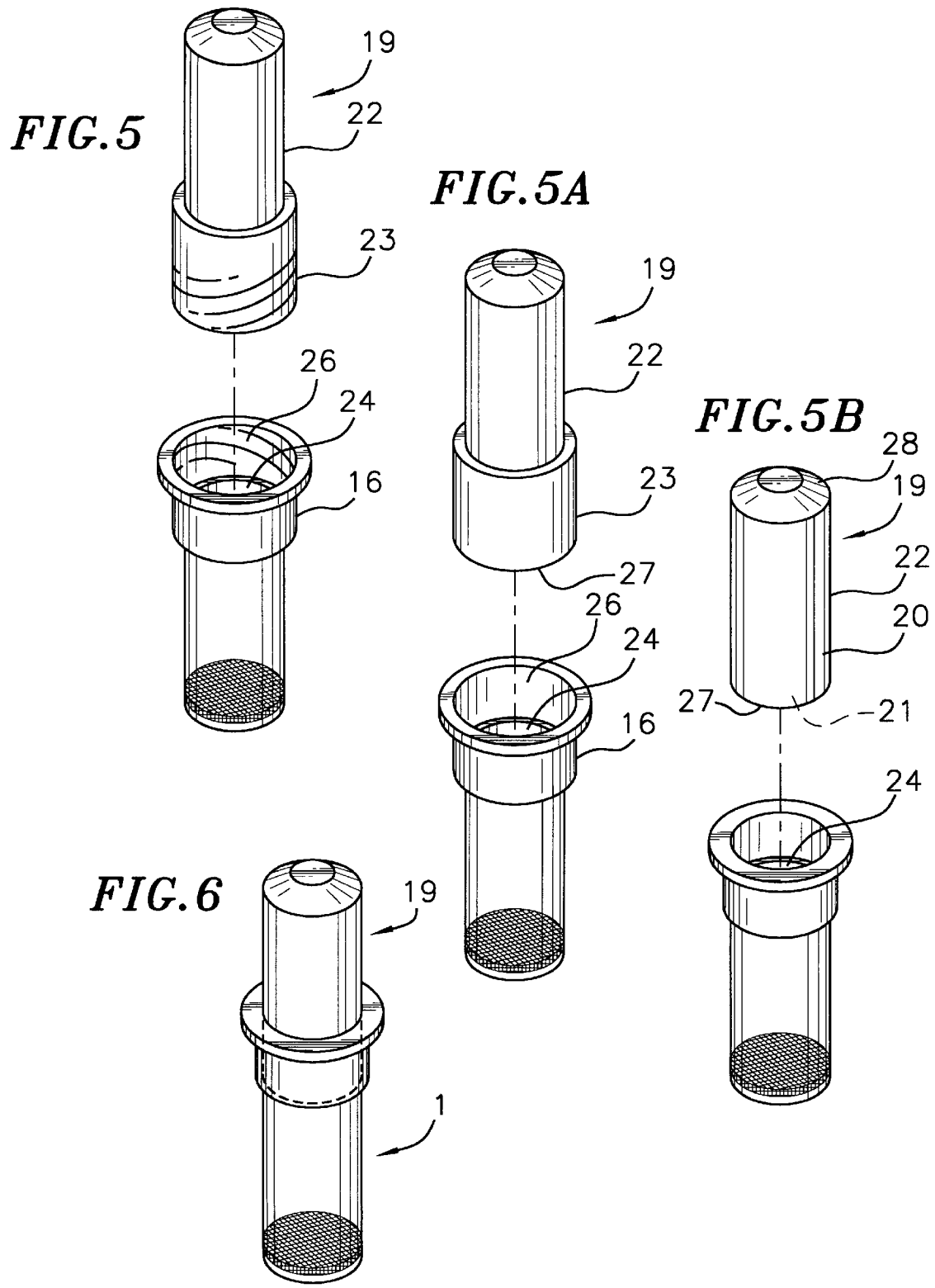

SPIN FILTER ASSEMBLY FOR ISOLATION AND ANALYSIS

BACKGROUND

This invention relates to the facilitation of the isolation and subsequent analyses or molecules or compounds, particularly proteins in various biological and non-biological solutions through the use of a specially designed spin filter assembly comprising of a spin filter and a container closure means to separate proteins or other desired compounds after being bound to solid binding matrices or resins. Spin filters are also known as microcentrifuge tube filters.

A conventional spin filter is generally a tube having an open top end and a filter means on the bottom end opposite the top end. The spin filter is generally adapted to fit within the upper portion of a standard centrifuge holder, a microcentrifuge tube or a centrifuge cup. the usage of spin filters for separation are largely dictated by the type of filters attached or laid on top of the bottom end of the spin filter. Examples of filters currently used with commercially available spin filters are ion exchange membranes which typically separates the proteins, on the basis of their charges, from low molecular weight contaminants such as salts, detergents and others; membranes with pore sizes in the micrometer or nanometer ranges for removal of particles, concentration of proteins, for buffer exchange, reduction or removal of salts or other low molecular weight contaminants which includes among others, non-incorporated labels, linkers and primers. Affinity membranes, on the other hand, are used to capture specific proteins.

The use of microcentrifuge tube containing filters or spin filter, that selectively separate one component or compound from another is disclosed in U.S. Pat. No. 4,683,058. Different commercial manufacturers have adopted the concept and are selling variations of the microcentrifuge tube filters or spin filter either as a stand alone unit or as a component of an assay kit. None of the available spin filters, however, provide the desired recovery, ease and speed of separation that the spin filter assembly of this invention provides.

The spin filter assembly of this invention is key to facilitating the isolation and assay or test of a desired compound in solution because of the shortened separation time required for isolation and testing. The spin filter assembly of this invention comprise of a tube having an open top end, a bottom end opposite the open top end, a body of a first length, an inner diameter and a first outer diameter, a filter means at the bottom end, the tube insertable to an upper portion of a centrifuge holder having a closed lower end, an open upper end, a length longer than the first length of the tube, and a second inner diameter greater than the first outer diameter of the tube; and, a container closure means that fits on top of the open end of the tube. The filter means at the bottom end of the tube is preferably a woven screen of a desired mesh size or a second filtering media on top of the woven screen. The tube with the filter means is herein referred to as the spin filter. In the claims, the spin filter is referred to as the tube of the spin filter. The spin filter with the container closure means is herein referred to as the spin filter assembly which is the object of this invention. The spin filter assembly allow for multiple sample analysis and eliminates the transfer of one suspension or solution from one container to the other which is currently accomplished through the use of a transferring device such as a pipet. The filter means and the filtering media for protein determination and isolation is preferably a low protein binding filter. The filtering media used in this invention is of a particular porosity and geometry in the form of a filter frit that is applied on the bottom of the tube or on top of a woven screen which is attached to the bottom end of the spin filter. A filter frit as used herein means a flat filter disk typically and preferably made of porous plastic material. The geometry, porosity and depth of the filter frit of this invention allows for unimpeded flow with minimal liquid retention thereby allowing rapid separation, washing and elution steps commonly employed in various assay methodologies for organic compounds, more particularly proteins. The filter frit used herein allows for quantitative analysis of a desired compound or protein which is not necessarily achievable with other filtering media. Quantitative analysis means determining the concentration of a component or compound with accuracy. Due to the property of the filter frit of this invention, the number of steps needed for washing and elution is also reduced. Washing as used herein means adding a washing solution to a precipitate, a solid matrix, bead or pellet obtained after centrifugation to form a suspension and recentrifuging the suspension to reisolate the precipitate, solid matrix, bead or pellet. The washing step removes or recovers compounds in solution occluded within the solid precipitate, bead or pellet. Assay as used here is synonymous to the meaning of analysis, determination or test. The assay may be directed to the determination of the amount, size, and expression level of the desired compound and to detect presence of modification or degree of interaction of the desired compound with other compounds.

It is an object of this invention to provide a rapid procedure for isolating and subsequently analyzing the isolated protein or other desired compound in solution.

It is also an object of this invention to provide a spin filter assembly that shortens the analysis by reducing the time required for separating a liquid from a solid component.

It is also an object of this invention to provide a spin filter assembly that shortens the analysis by reducing or eliminating the transfer time of liquid or solid suspensions from one tube to the other.

It is also an object of this invention to provide a spin filter assembly that is adaptable for multiple sample processing.

It is also an object of this invention to provide a means for improving the accuracy of a determination, test or assay by reducing or eliminating device driven transfers from one container to the other and using a low binding filter media.

It is a further object of this invention to provide an analytical kit that is a complete system having the spin filter assembly as a component, for a fast and simple process of isolating and analyzing a desired compound.

SUMMARY

This invention relates to a rapid method for isolating and determining a desired compound in solution, preferably proteins or antigens, after it is bound to a solid binding matrix, through the use of a spin filter assembly having a combination of a low binding filter, that is, a filter with minimal or no affinity to the desired compound and a container closure capable of holding a desired volume of solution or suspension. The spin filter assembly of this invention comprise of a tube having an open top end, a bottom end opposite the open top end, a body of a first length, an inner diameter and a first outer diameter and a filter means at the bottom end, the tube insertable to an upper portion of a centrifuge holder having a closed lower end, an open upper end, a length longer than the first length of the tube, and a second inner diameter greater than the first outer diameter of the tube; and, a container closure means that fits on top of the open end of the tube. The container closure means is unique and allow for rapid and quantitative transfers of solutions and suspensions from one container to the other. Quantitative transfer herein means transfer with minimal loss. The filter means at the bottom of the tube or the spin filter may be a filtering media such as a filter frit or a woven screen of a desired mesh size, or a combination of a woven screen at the bottom of the spin filter with a filtering media, a filter frit, laid on top of the woven screen. The woven screen or the filter frit is of a certain porosity, composition, geometry and dimension so as to cause low sample and buffer volume retention and rapid separation without sacrificing accuracy in quantitation and yield of the desired compound, particularly proteins. Quantitation herein means determination of the amount or quantity of the desired compound. The spin filter assembly can vary in size, from a microtube to a large cylinder depending upon the application of choice and the amount of the desired compound present per volume of solution. The spin filter assembly of this invention, facilitates and makes possible the analytical process for determining proteins by immunoprecipitation, affinity binding, protein-protein interaction and other methods based on interactions between molecules. The spin filter assembly may be made a component of a sample preparation and assay kit which comprises, in addition to the spin filter assembly, a solid binding matrix for the desired compound, a washing solution, an elution solution for releasing the desired compound from the binding matrix, and optionally, a solubilizing or lysing solution if the desired compound is not in solution and a holder for the spin filter assembly. Holders for the spin filter assembly are usually commercially available as standard centrifuge tube. Covalent crosslinking of the binder to the solid matrix may be incorporated into the process if a purer compound or a more accurate test result is desired. The process of sample preparation and analysis is generally uniform, lending itself to routine process steps, a property desirable for multiple sample analyses, comprising the steps of solubilizing or releasing a desired compound from the cell or tissue with a lysing or solubilizing solution, the released compound herein referred to as lysate or cell lysate solution which contain the desired compound in solution; removing contaminating soluble and insoluble matters from the solution containing the desired compound; binding the desired compound in solution to a solid binding matrix having a binder reactive to the desired compound; resulting into a suspension containing a desired matrix bound compound transferring the suspension to the spin filter 1; isolating or separating the desired matrix bound compound from the suspension by centrifugation with the spin filter assembly comprising of a tube having an open top end, a bottom end opposite the open top end, a body of a first length and a first outer diameter and a filter means at the bottom end, the tube insertable to an upper portion of a centrifuge holder having a closed lower end, an open upper end, a length longer than the first length of the tube, and a second inner diameter greater than the first outer diameter of the tube; and, preferably a container closure means that fits on top of the open end of the tube with the filter means or the spin filter; and, eluting the desired matrix found compound from the solid binding matrix with an elution solution introduced into the tube of the spin filter assembly containing the desired matrix bound compound. The eluted compound, usually a protein, can thereafter be analyzed typically for its concentration, biological activity and association with other proteins by several known analytical methods. The same process may be used for analysis of the desired compound already in solution by skipping the lysis step for solubilizing or releasing the desired compound from their matrices such as cells and tissues.

BRIEF DESCRIPTION OF THE DRAWING

FIG. 1A is a cross sectional view of the spin filter inside a centrifuge holder taken at a point halfway its length.

FIG. 5 is a perspective view of a container closure means threaded to the top open end of a spin filter.

FIG. 5A is a perspective view of a container closure means friction or snapped fit into the cylindrical strip of a spin filter.

FIG. 5B is a perspective view of a container closure means without a second cylindrical strip friction fit into the cylindrical strip of a spin filter.

FIG. 6 is a perspective view of the container closure means fit into the spin filter with the inner diameter of the spin filter in alignment with the inner diameter of the container closure means.

DETAILED DESCRIPTION OF THE INVENTION

Figure 1:
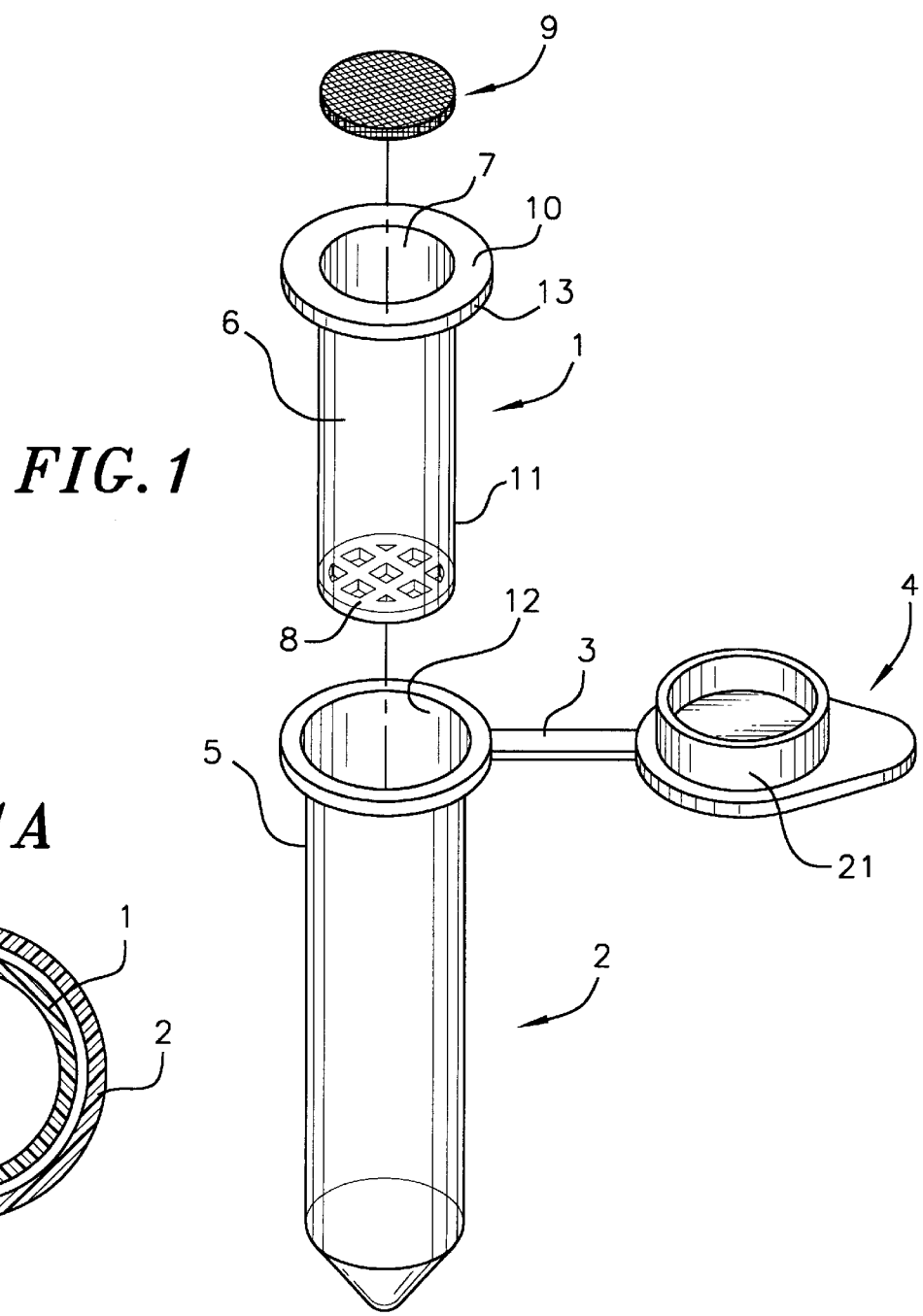
FIG. 1 is an exploded perspective view of a spin filter without a cylindrical strip in relation to the centrifuge holder.
Figure 2:
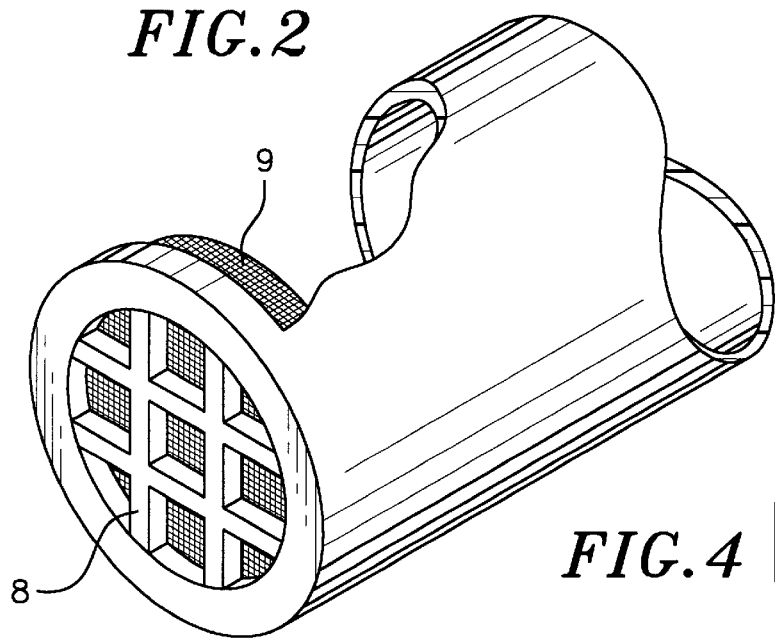
FIG. 2 is a partial perspective view of the filter frit in relation to the screen on the spin filter.
Figure 4:
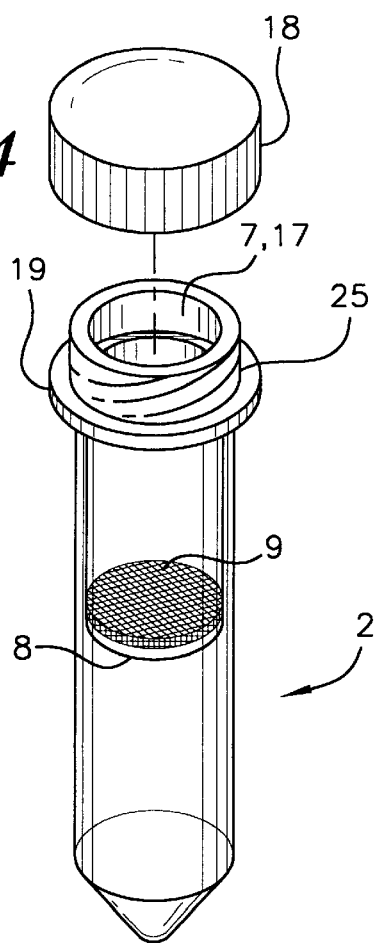
FIG. 4 is a perspective view of a threaded capped spin filter shown inside a centrifuge holder.
Figure 3:
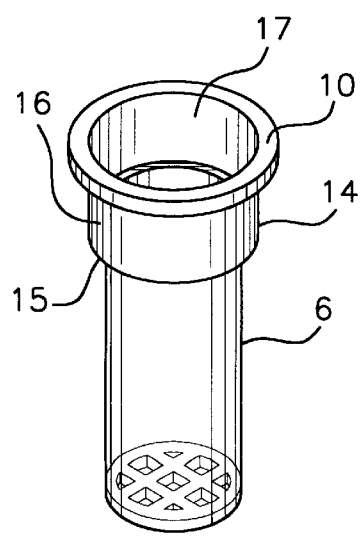
FIG. 3 is a perspective view of a spin filter with a cylindrical strip.

The spin filter 1 of this invention is insertable to a centrifuge holder 2 having a closed lower end and an open upper end such as a centrifuge tube or a centrifuge cup, as shown in FIG. 1, which is in turn adapted to fit within a chamber of a centrifuge rotor. When the spin filter inside the centrifuge holder is spun within the chamber, materials larger than the pore size of the screen or the filtering media, a filter frit, at the bottom of the spin filter are retained inside the spin filter. The filter frit can also be used in conjunction with the screen. The shape of the centrifuge holder is not critical, but is preferentially cylindrical, so long as the centrifuge holder allow the spin filter to slide easily in axial alignment within its upper portion 5 as shown in FIG. 1. The spin filter 1 is preferably a tube comprising a cylindrical body 6 of a first length less than a second length of the centrifuge holder 2 and a first outer diameter 11 less than a second inner diameter 12 of the centrifuge holder 2 as shown in FIGS. 1 and 1A. The cylindrical body 6 of the spin filter 1 has two ends, an open top 7 and a bottom end, the bottom end 8 preferably having a screen disposed in the bottom of the cylindrical body. The screen is typically of a woven mesh. The mesh size varies depending upon the particle size of the solid to be retained. For finer filtration, a filter frit 9, is introduced and usually fits on top of the screen located at the bottom 8 of the spin filter as shown in FIGS. 2 and 4. A usable spin filter with a bottom screen but without the filter frit is Forensic Micro-Spin sold by PGC Scientific of Gaithersburg, Md. 20898 under catalog number 34-0480. The spin filter with the filter frit 9 is used when the solid binding matrix, such as a protein binding matrix, has a mesh size smaller than the screen at the bottom end 8 of the spin filter. The filter frit 9 is generally made of a porous low protein binding material such as polyethylene and polypropylene and combinations of these formulations and the like. The preferred filter frit of this invention is sold by Porex Technologies Corporation and identified as XM-1273. The filter frit is preferably a flat sintered disc made of a porous ultrahigh molecular weight polyethylene material of precisely defined particle size distribution. The filter frit is prepared by compacting the polyethylene polymeric material to a particular density, then sintered by heating in a circulating air oven to cause the surfaces of the individual polymer particles to fuse at their contact points thereby forming the porous moulding, here in a form of a flat sheet, subsequent to careful cooling after the sintering process. This filter frit has a thickness of 0.03–0.04 inches and an air flow rate of 818–2250 ml/min when tested at a set inlet pressure of 1.2 inches of water through an area of 0.75 inches of a one inch sample disc. Laterally protruding lip or flange 10 having a third outside diameter 13 greater than the second inner diameter 12 of the centrifuge holder 2 may be attached or molded around the top open end 7 of the cylindrical body 6 of the spin filter to seal the centrifuge tube when the spin filter is inserted inside the centrifuge holder 2. To position the spin filter at a predetermined upper portion of the centrifuge holder, instead of having a flange on the top open end of the cylindrical body 6, it is preferable for the top open end 7 of the cylindrical body 6 to open up and connect to a bottom end 15 of a cylindrical strip 16 as shown in FIG. 3. The cylindrical strip 16 has a fourth outer diameter 14 greater than the second inner diameter 12 of the centrifuge holder 2. The point at which the cylindrical body 6 and the wider cylindrical strip 16 joins together will consequently sit on top of the centrifuge holder 2 because the fourth outer diameter 14 of the cylindrical strip 16 is greater than the second inner diameter 12 of the centrifuge holder 2 thereby sealing the centrifuge holder and preventing the spin filter from dropping into the bottom of the centrifuge holder during centrifugation. The height of the cylindrical strip 16 is approximately an eight to a third of the entire length of the spin filter 1 as shown in FIG. 3. The inner diameter of the cylindrical strip 16 is preferably greater than the inner diameter 24 of the cylindrical body of the spin filter. When the spin filter is designed with a second cylindrical strip 16, the lip or flange 10 is usually attached or molded around the top open end 17 of the cylindrical strip 16 which then becomes the open top end of the spin filter 1. The flange 10 provides ease for handling the spin filter especially when it is repeatedly inserted or removed from a centrifuge holder connected to a cap 4 by a flexible connecting member 3 shown in FIG. 1 where the cap 4 is used to cover the spin filter instead of the centrifuge holder during centrifugation. In addition to or instead of a lip or flange 10, projecting tabs (not shown) can be provided on the periphery of the top opening 7 for spin filters without a cylindrical strip or 17 for spin filters with a cylindrical strip, to facilitate removal of the spin filter from the centrifuge holder. The spin filter assembly of this invention comprise in addition to or in combination with the spin filter described above, a closure means for covering the spin filter. A closure means is advisably used during the assay especially when the samples are hazardous, releases air borne bacteria and viruses, and/or volatile. The closure means can be the cap 4 of the centrifuge holder 2 capping the top opening 7 or 17 of the spin filter instead of the top opening of the centrifuge holder 2. Alternately, the closure means can be an ordinary cap 18 with a closed top surface and an open bottom end having means to attach to the top opening 7 or 17 of the spin filter as shown in FIG. 4. The cap 18 can lock, snap fit, friction fit, thread or screw on the top opening of the spin filter. The unique feature of the spin filter assembly of this invention is the closure means that is itself a container, hereinafter referred to as container closure 19 that can hold a desired volume of solution or sample and is of the same geometrical shape as the body of the spin filter. For example, a spin filter with a cylindrical body 6 will have a cylindrical container closure 20 having an inner diameter 21 and an outer diameter 22 with one end 28 closed and the other end 27 opened for attachment to the spin filter, that is, to lock into, snap fit, friction fit, thread or screw on to the spin filter as shown in FIG. 5B. A cylindrical container closure, like the spin filter, may have a second cylindrical strip 23 on the open end of the cylindrical container closure 20 as shown in FIGS. 5 and 5A. Other known means of attaching a container closure to an open top surface can be applied as well so long as it can be repeatedly attached and detached. FIG. 5 shows a container closure with the second cylindrical strip 23 of the closure means threaded to the cylindrical strip 16 of the spin filter. FIG. 5A shows a container closure friction or snapped fit into the cylindrical strip 16 of the spin filter. On the use of a container closure 19, for example, in a cylindrical container closure 20, to function as desired, it is important for the inner diameter 21 of the container closure to align and match well with the inner diameter 24 of the tubular body of the spin filter 1 as shown in FIG. 6 to form a continuous unit having a continuous longitudinal inner wall from the container closure to the spin filter. If the spin filter is not cylindrical, the inner walls of the corresponding closure must align and match with the inner wall of the spin filter. If the inner walls are not well aligned, any break on the surface of the inner wall will cause some solid binding matrix or solution to enter or deposit into the break areas, resulting in a poor assay. The container closure may also attach to the spin filter on the upper outside surface 25 in the same manner as shown by example, the attachment of cap 18 to the spin filter in FIG. 4 or on the upper inside surface 26 of the spin filter as shown in FIGS. 5, 5A and 5B. When a separate threaded or plug cap 18 or a container closure 19 is used for covering the spin filter, the outer diameter of the cap 18 or the cylindrical strip 16 of the spin filter will seal the centrifuge holder and serve the same purpose as the projecting tabs or flange 10.

Although it is preferable to use the spin filter assembly having a container closure, a spin filter with a cap 4 or 18 may be used for protein preparations and analyses but this is more tedious because separate containers and transfer devices are needed. For protein preparations utilizing volumes in the microliter ranges, the spin filter is inserted within an upper portion of a centrifuge holder 2, preferably a microcentrifuge tube, and capped. Examples of microcentrifuge tubes adaptable as centrifuge holders for the small volume spin filter 1 are disclosed in U.S. Pat. No. 4,683,053 as standard centrifuge tubes 50 and 93 and in U.S. Pat. Nos. 4,755,356 and 5,382,408. The closed bottom portion of these centrifuge tubes need not be conical in shape so long as the spin filter 1 can be accommodated or inserted within the upper portion 5 of the centrifuge holder 2. For larger volumes, a spin filter assembly with preferably a peripheral lip or flange 19 is generally inserted into a large centrifuge holder 2 for ease of handling as shown in FIG. 4. The spin filter is preferably made of a plastic material such as polypropylene, polycarbonate, cellulose acetate, polyvinylchloride, polyvinylacetate, polyethylene, nylon and derivatives of nylon, polyurethane, ethylene vinyl acetate, polysulfone and combinations of any of these formulations.

The spin filter assembly as used herein may be incorporated as a component of a protein assay or purification preparation kit. Other major components of the kit includes a solid binding matrix, a washing solution, an eluting solution and a solubilizing or lysing solution if the protein is not in solution. A holder for the spin filter assembly may also be provided but these are usually standard centrifuge tubes which are commercially available. For immunoprecipitation and process involving cell lysis, preimmune serum and protease inhibitors may also be supplied with the kit.

Solid binding matrices, as exemplified herein by a protein binding matrix, are generally prepared by coating, binding or linking a protein, a peptide, an organic or inorganic chelator, or other reactive organic compounds on the outer surface of a solid support such as cross-linked dextran, glass bead, silica, cross-linked agarose, and other support materials known in the art. Preparation of specific binding matrices used for isolating desired compounds or substances in solution are known in the art. The compounds bound to the solid matrix, referred to herein as binder, must be of such composition or structure so as to be reactive to and specifically bind the desired compound, which is in the example of this invention, a protein in solution. By way of examples, to isolate a given protein in solution, such as an antibody, an antigen or an antibody-antigen complex, affinity matrices such as Protein A, Protein G, an antigen known to bind the antibody or vice-versa or antigen-antibody complex bound to Protein A and Protein G matrices may be used as the binder. Metal chelators such as iminodiacetic acid resin or nickel nitrilotriacetic acid resin are used to isolate histidine tagged proteins. Glutathione bound to a solid matrix can be used to isolate glutathione S-transferase (GST) fusion proteins. N-hydroxysuccinimide-activated or cyanogen bromide activated agarose matrix can be used to covalently bind proteins with reactive amino groups. It is too numerous to list herein, all known specific protein binders for a specific protein but one skilled in the art are familiar with these and their respective applications.

In the same light, it is impossible to name all the protein eluting solutions that can be used as a component of the kit. The nature of the eluting solution will vary according to the characteristics of the bound protein and the chemical nature and affinity of the binder to the attached protein. Eluting solutions usually may contain reagents that displace the bound compound, here a protein. A washing solution, on the other hand, is dictated by methods of separating the desired protein from other contaminants. The separation is affected by such factors as ionic strength, pH, salt composition, presence of detergents and the general chemical characteristics of the washing solution.

The proposed process herein employing the spin filter assembly for the preparation of the protein sample for analysis or assay, follow the general uniform steps of solubilizing a desired compound, herein a protein by way of example, with solubilizing agents such as solutions containing varying concentrations of detergents and/or chaotropic salts such as guanidine and urea to bring the protein in solution, if the compound is in an insoluble form; removing any soluble and insoluble contaminating matters from the protein solution by affinity binding, centrifugation or filtration; binding the desired protein to a solid protein binding matrix; isolating the matrix bound protein by transferring the mixture containing the protein bound to the solid protein binding matrix to a spin filter; inserting the spin filter into a centrifuge holder and centrifuging the spin filter; and, eluting the desired protein from the solid protein binding matrix. The eluted protein can then be analyzed for purity, association with another protein, biological activity and/or concentration by known analytical methods such as spectrophotometric, spectrometric and various electrophoretic measurements, autoradiography, chromatography, immunoblotting, radioactivity, enzymatic determinations and others. Variations in the main scheme of the process lies mainly in the number of process steps for the solubilization or release of the desired protein into the sample solution before the protein is made to react with the protein binder on the surface of the solid matrix. The lysing or solubilization step is omitted when the desired protein is already in solution.

The following examples illustrate the usage of the spin filter and how it facilitates, increase accuracy, shorten the time and allow processing and analyses of multiple samples using the general process scheme. The immunoprecipitation process scheme described for the determination of a selected compound, here for example, a protein present in cells or tissues, may be packaged and offered for use as a test kit. Immunoprecipitation as used herein is a technique for characterizing or identifying an antigen by separating the antigen in a complex mixture using a bound antibody.

Example One illustrates the immunoprecipitation process without an immobilization step. Example Two illustrates the immunoprecipitation process with an immobilization step. Immobilization herein means the covalent chemical crosslinking of a compound, a binder, on the surface of a solid matrix. The crosslinking of an antibody to a Protein A/G solid binding matrix is illustrated in Example Two. The protein, having affinity to the antibody, then binds to the crosslinked Protein A/G matrix. Protein A/G solid binding matrix is a mixture of Protein A and Protein G solid binding matrices or Protein A and Protein G covalently attached to the same binding matrix. In general, equal amount of Protein A binding matrix and Protein G binding matrix are used. When the antibodies are merely bound to the Protein A/G by affinity and not immobilized, during the elution step, there is a possibility that the eluents will also contain protein-antibody complexes or unbound antibodies together with the protein of choice. Crosslinking antibodies to Protein A/G eliminates the contaminating antibodies. Incorporation of the immobilization step into the process, despite of its advantages, are usually not done because the process is tedious. However, immobilization becomes more feasible with the use of the spin filter assembly. Repeated and stepwise reactions and separations can be carried out with ease because transfers of suspensions or solutions from one container to the other using external transferring devices are eliminated. Additionally, separation time is further shortened because of the filtering characteristics of the spin filter. The binder and immobilization reagents may be provided with the kit if immobilization is desired. Variations as to the actual chemicals and reagents used for isolating and/or assaying varying compounds using the spin filter assembly with the general process scheme described herein are within the scope of this invention.

EXAMPLE ONE

Protein Isolation and Analysis by Immunoprecipitation.

The cells, tissues, protein extracts and the like, containing the desired protein are placed in a suitable container and lysed with a protein solubilizing solution, usually a buffer solution, with such a volume as to have a final total protein concentration in the range of 1–5 mg/ml. The lysed sample is herein referred to as cell lysate solution. The lysing solution used in this example is 1% Triton X-100, 150 mM NaCl, 20 mM Tris, at a pH of approximately 8.0, hereinafter referred to as Solution A. NaCl is sodium chloride and Tris is Tris-(hydroxymethyl)aminomethane. Solution A is used when it is desired to preserve protein-protein interaction, antigen-antibody interaction and enzyme activity. Solution A can be substituted with other buffered solutions in other applications, depending upon the type of protein interaction involved in the sample. The main requirement for such buffered solution is that it be non-denaturing to the protein to be isolated and analyzed. A mixture of protease inhibitors is preferably added to Solution A to inhibit the activity of various types of proteases in the cell lysate. Suitable protease inhibitor cocktails commercially available include Protease Inhibitor Cocktail sold by Calbiochem-Novabiochem Corporation, of San Diego, Calif. 92121 under catalog number 539131-B and "Complete", Protease Inhibitor Cocktail Tablets, sold by Boehringer Mannheim of Indianapolis, Ind. 46250 under catalog numbers 1 697 498 and 1 836 145. If the desired protein is an insoluble or a membrane protein or if it is immaterial to preserve protein-protein interaction, antigen-antibody interaction and enzyme activity, the cells are preferably lysed by a solution containing 0.1% sodium dodecyl sulfate (SDS), 1% sodium deoxycholate, 1% Triton X-100, 150 mM NaCl, 2 mM ethylenediaminetetracetate (EDTA), and 20 mM Tris at pH of approximately 8.0, hereinafter referred to as Solution B. The lysed cells or cell lysate suspended in the various solutions described are then centrifuged, typically at approximately 25,000×g for at least 15 minutes to remove any aggregates and cell debris from the solubilized protein. As practiced in the art, after centrifugation, the clarified solution is transferred to a second container while the insoluble cell debris that gets packed in the bottom of the initial container, usually the centrifuge tube, is discarded with the container. The proteins in the clarified cell lysate solution is incubated preferably at ambient or room temperature with a suspension of solid Protein A/G binding matrix, herein referred to as solid binding matrix containing bound immunoglobulin to remove non-specific proteins in the lysate that can bind to the solid protein binding matrix and contaminate the desired protein. The solid binding matrix used here is prepared by incubating the matrix with preimmune serum at a ratio of three part preimmune serum to one part of Protein A/G solid binding matrix by volume. Preimmune serum is a serum obtained from the same specie producing the antibody reagent used in the assay. After the reaction, the solid binding matrix is separated from the resulting solution referred to as isolated cell lysate, using the spin filter where the cell lysate is captured into the centrifuge tube holding the spin filter.

Suitable Protein A and Protein G solid binding matrices are available commercially such as "Immobilized Recomb" Protein A sold by Pierce at Rockford, Ill. under catalog number 20365 and 20366; Protein G or A Agarose from Calbiochem-Novachem of San Diego, Calif. under catalog numbers 539205 and 539207; Protein A or Protein G from Sigma of St. Louis, Mo. under catalog numbers P 1052, P3036, P0932, P7786 and P7700; and, "Protein G Sepharose" 4 Fast Flow or "Protein A Sepharose" Fast Flow from Pharmacia Biotech of Piscataway, N.J. under code number 17-1279-02 and 17-0618-02. For solid Protein A/G matrices, a combination of Protein A and G Sepharose is preferred and the suspension suitable for use in this example is prepared by bringing a Protein A Sepharose and Protein G Sepharose of equal proportions to a uniform suspension, washed several times with Solution A by repeated reconstitution and recentrifugation, and then suspending the resulting solid Protein A/G Sepharose or solid binding matrix in Solution A.

The isolated contaminant free cell lysate is herein preferably transferred to a container closure 19 of the spin filter assembly instead of a second container and incubated with a solid protein binding matrix, herein a Protein A/G Sepharose having on its surface, bound antibodies reactive to the desired protein in the cell lysate. This illustrated reaction typically takes approximately 60 minutes with gentle agitation but the reaction time may vary depending upon the affinity of the protein to the antibody. Alternatively, the desired protein in the isolated cell lysate is first reacted with a reagent in solution, here an antibody, followed by reacting or binding the reagent bound protein with the solid protein binding matrix reactive with the reagent or the antibody. A suitable solid protein binding matrix for this alternate step is Protein A/G matrix without the antibody bound to its surface. Binding conditions depend upon the nature of the desired protein to be isolated and the degree of affinity of the reactants to each other, that is, in this case, the affinity of the antibody to the antigen. Typically, for a protein antigen-antibody, binding is done at room temperature for approximately 60 minutes, but binding can range from 15 minutes to 24 hours. The suspension is preferably shaken or stirred during the binding reaction to keep the solid protein binding matrix in suspension. When a container closure 19, instead of a typical test tube, is used as the holder or vessel for the reaction, the spin filter 1 or the tube of the spin filter assembly is attached upside down, i.e. with the bottom filter media on top, to the top opening of the container closure 19. After the reaction and before centrifugation, the spin filter with the container closure, that is, the spin filter assembly, is simply inverted, gently tapped and inserted into a centrifuge holder 2. The resulting suspension which contains the desired matrix bound protein on the surface of the solid protein binding matrix is centrifuged. The spin filter 1 prior to use or attachment to the container closure 19 is preferably prewashed with Solution A and the washing solution removed by centrifugation. If the binding reaction was carried on a different holder or tube other than the container closure 19 of the spin filter, the resulting suspension which contains the desired matrix bound protein on the surface of the solid protein binding matrix is transferred to the prewashed spin filter 1 by external transferring devices such as a pipet and capped. Without the container closure, the only advantage in using the spin filter is the speed by which the separation can be accomplished through the use of the proposed filter media, the filter frit described above. Use of the container closure 19 of the spin filter assembly, deletes the step of transferring the suspension from one holder or tube to the spin filter which is usually done through pipetting and also provides a more accurate and quantitative transfer of the suspension or solution, thereby avoid loss of the desired compound, herein a protein, because the spin filter with the container closure is simply inverted prior to centrifugation. If the mesh size of the solid protein binding matrix is larger than those of screen at the bottom 8 of the spin filter 1, the suspension may be centrifuged without the filter frit 9. However, commercially available Protein A and G solid binding matrices and most solid protein binding matrices, typically have mesh sizes smaller than those of screen, thereby requiring that a filter frit 9 be placed directly on top of the screen at the bottom 8 of the spin filter 1 prior to prewash and subsequent transfer and centrifugation of the suspension containing the desired matrix bound protein as shown in FIGS. 2 and 4.

The spin filter 1 is placed inside a centrifuge holder, and centrifuged for at least 30 seconds, usually not exceeding three minutes, at approximately 16,000×g. The highly porous characteristic of the filter frit on the spin filter allows this rapid separation of the isolated cell lysate from the desired proteins bound to the solid protein binding matrix herein also referred to as desired matrix bound compound. The solution passing through the filter frit of the spin filter into the centrifuge holder, is discarded. The solid protein binding matrix with the bound protein of interest or desired matrix bound compound is retained by the filter frit of the spin filter 1. The solid protein binding matrix above is washed by adding a small volume of Solution A or B to the spin filter and recentrifuging the solid matrix for another minute, with the resulting flow through discarded. After washing the solid protein binding matrix above, the spin filter 1 is preferably transferred to a new centrifuge holder to avoid any contamination from residuals, compounds other than the desired protein, that may be present in the original centrifuge holder. The desired protein is then eluted from the solid protein binding matrix or desired matrix compound. For analytical purpose, the protein eluting buffer is mixed with the sodium dodecyl sulfate solution that will be used to analyze the protein by polyacrylamide gel electrophoresis. The protein elution buffer illustrated here is a solution containing 2% sodium dodecyl sulfate or SDS, 10% glycerol, 120 mM of 2-mercaptoethanol, 0.005% bromophenol blue, 50 mM Tris-HCL at a pH of approximately 6.8. Elution is done by incubating the protein bound to the solid protein binding matrix or desired matrix compound in the spin filter for approximately 15 minutes at ambient or room temperature, usually around 21 degrees centigrade, with the elution buffer, followed by centrifugation for approximately one minute. If preservation of the activity of the eluted protein is desired, the bound protein is eluted with a non-denaturing reagent which displaces the protein from the antibody. Examples of such procedures include the displacement of a bound protein from a monoclonal antibody through the use of polypeptides having the same sequence as the epitope sequence of the desired protein or eluting the bound protein from a monoclonal antibody by using an elution buffer with a pH ranging from 3–5. The eluted protein is caught in a new centrifuge holder 2 and analyzed using various analytical methods suited for the information or type of result sought such as gel electrophoresis followed by autoradiography, chromatography, immunoblotting, gel scanning and the like, radioactivity determination, and other methods known in the art.

EXAMPLE TWO

Part A
Immobilization of Antibody to Protein A/G Solid Binding Matrix.

The Protein A/G solid binding matrix is incubated in a container closure 19 of the spin filter assembly with a specified amount of specific antibody, polyclonal or monoclonal. The volume ratio of the Protein A/G suspension to the antibodies is determined separately because each antibody will have its own specific binding affinity and capacity for the particular Protein A/G solid binding matrix used. Incubation is typically done for 30 minutes under gentle agitation at room temperature.

The spin filter 1 is then attached upside down to the open end 27 of the container closure 19 and the spin filter assembly is inverted and inserted into a centrifuge holder 2. The spin filter assembly containing the suspension is centrifuged for at least 30 seconds, not exceeding 3 minutes at 5000×g. This step combines both the transferring of the suspension from the container closure 19 to the spin filter 1 and the separation of the Protein A/G solid binding matrix containing the bound antibodies from the other proteins in solution. Protein A/G solid binding matrix with the specific antibody bound to its surface obtained after the above step is hereafter referred to as Ab-Protein A/G solid binding matrix. The Ab-Protein A/G solid binding matrix is then washed, usually two times with 100 mM sodium borate, pH 8.0 to further remove non-specific protein contaminants. The Ab-Protein A/G solid binding matrix is then chemically crosslinked by the addition of 10 mM dimethylsuberimidate solution in sodium borate, pH 8.5 and the reaction allowed to proceed for approximately 30 minutes at room temperature. A volume of 50 microliter crosslinking reagent is usually sufficient for a 10 microliter volume of Ab-Protein A/G solid binding matrix. Other crosslinking reagents known in the art such as glutaraldehyde, disuccinimidyl glutarate and others can also be used. The crosslinking reaction is stopped by the addition and reaction with 0.5–1.0 M ethanolamine in sodium borate solution, pH 8.5. A volume equal to the volume of the crosslinking reagent is typically used and the reaction is also typically done at room temperature.

After cross-linking, the resulting crosslinked Ab-Protein A/G solid binding matrix, hereinafter referred to as xAb-Protein A/G solid binding matrix, is then washed approximately two times with a buffer to remove the excess reagents. Solution A is preferably used as the buffer for washing. The process steps of cross-linking, stopping the reaction and washing the Ab-Protein A/G solid binding matrix are conveniently performed using the spin filter assembly.

Part B
Protein Isolation and Analysis by Immuno-precipitation.

The spin filter containing the xAb-Protein A/G solid binding matrix from Part A is reacted with the desired compound contained in the isolated cell lysate obtained in the same manner as described in Example One. A 100 microliter of the isolated cell lysate is usually reacted with 20 microliter of xAb-Protein A/G solid binding matrix prepared in Part A of this example. The isolated cell lysate herein refer to the solution obtained after lysis, removal of the aggregates and preincubation with preimmune serum containing Protein A/G as described in Example One.

After the addition of the isolated cell lysate, the spin filter 1 is immediately capped or preferably attached to the container closure 19 having a volume capacity sufficient to hold the reaction mixture. The spin filter assembly is inverted, inserted into a centrifuge holder 2 and spun for approximately one minute at room temperature to transfer the suspension mixture, the xAb-Protein A/G solid binding matrix and the isolated cell lysate, from the spin filter to the container closure. The binding of the desired compound in the cell lysate to the xAb-Protein A/G solid binding matrix is accomplished by incubating the suspension mixture for a certain specified time and temperature. The time and temperature is determined separately because this will vary for each compound and each binding matrix used. However, a reaction time of approximately one to two hours at room temperature is usually sufficient.

After the reaction, the spin filter is removed from the assembly and the suspension mixture in the container closure is diluted to approximately three times its volume with a buffered solution, preferably, Solution A. After dilution, a new spin filter 1 is attached upside down to the container closure 19, inverted and inserted into a centrifuge holder 2. The spin filter assembly is spun for approximately one minute to transfer the suspension mixture from the container closure to the spin filter and separate the desired matrix bound compound, here a protein bound to the xAb-Protein A/G solid binding matrix, from the suspension mixture. The isolated protein bound to the xAb-Protein A/G solid binding matrix or desired matrix bound compound above is washed, typically twice, before the desired compound, here a protein, is eluted from the xAb-Protein A/G solid binding matrix. Elution of the desired compound is accomplished in the same manner described in Example One.

Any compound or substance already in solution or that can be solubilized and subsequently bound specifically to a solid matrix of such rigidity as to withstand the centrifugal force applied for separating a liquid supernatant from a solid matrix may be separated and determined by this method.

While the embodiments of the present invention have been described, it should be understood that various changes, adaptations, and modifications may be made therein without departing from the spirit of the invention and the scope of the claims.

What is claimed is:

1. A spin filter assembly for rapid isolation and/or determination of a desired compound in a solution, comprising:
   a tube having an open top end, a bottom end opposite the open top end, a body of a first length, an inner diameter, a first outer diameter and a filter means at the bottom end, the tube insertable into an upper portion of a centrifuge holder having a closed lower end, an open upper end, a length longer than the first length of the tube, and a second inner diameter greater than the first outer diameter of the tube; and, a container closure means having an inner diameter, an outer diameter, an open end and a closed end, the open end fitting on top of the open end of the tube in a manner aligning the inner diameter of the container closure with the inner diameter of the tube, the container closure means hold a desired volume of solution.

2. The spin filter assembly of claim 1 wherein the spin filter assembly is made of a plastic material.

3. The spin filter assembly of claim 1 wherein the filter means is a porous low binding filter frit made of a material selected from the group consisting of polyethylene, polypropylene and combinations of polyethylene and polypropylene.

4. The spin filter assembly of claim 3 wherein the filter frit is a flat sintered disc made of a porous ultrahigh molecular weight polyethylene material.

5. The spin filter assembly of claim 4 wherein the filter frit has a thickness of 0.03–0.04 inches and an air flow rate of 818–2250 ml/min when tested at a set inlet pressure of 1.2 inches of water through an area of 0.75 inches of a one inch sample disc.

6. The spin filter assembly of claim 1 further comprising a cylindrical strip connected to the open top end of the tube, the cylindrical strip having a fourth outer diameter greater than the second inner diameter of the centrifuge holder.

7. The spin filter assembly of claim 1 wherein the tube of the spin filter assembly has a geometrical shape that can slide easily in axial alignment to the upper portion of the centrifuge holder.

8. The spin filter assembly of claim 7 wherein the container closure means have the same geometrical shape as the tube.

9. The spin filter assembly of claim 1 further comprising a cylindrical strip on the open end of the container closure.

10. The spin filter assembly of claim 9 wherein the inner diameter of the container closure means align and matches with the inner diameter of the tube.

11. A sample preparation and assay kit comprising the spin filter assembly of claim 1, a solid binding matrix, a washing solution, an elution solution, and optionally, holder for the spin filter and a solubilizing solution.

12. The kit of claim 11 further comprising an antibody solution.

13. The kit of claim 11 further comprising a preimmune serum.

14. The kit of claim 11 further comprising a binder which is reactive to a desired compound.

15. A method of using a spin filter assembly of claim 1, the assembly comprising a tube having an open top end, a bottom end opposite the open top end, a body of a first length, an inner diameter, a first outer diameter and a filter means at the bottom end, the tube insertable into an upper portion of a centrifuge holder having a closed lower end, an open upper end, a length longer than the first length of the tube, and a second inner diameter greater than the first outer diameter of the tube; and, a container closure means having an inner diameter, an outer diameter, an open end and a closed end, the open end fitting on top of the open end of the tube in a manner aligning the inner diameter of the container closure with the inner diameter of the tube, the container closure means adapted to hold a desired volume of solution, for greater accuracy and rapid isolation of a compound bound to a solid binding matrix thereby enabling the processing and analyzing of multiple samples, comprising the steps of:
   a) performing a binding of a desired compound in solution with a solid binding matrix in the container closure of the spin filter assembly resulting into a suspension containing a desired matrix bound compound;
   b) attaching the tube of the spin filter assembly on top of the container closure by aligning the open top end of the tube with the open end of the container closure;
   c) inverting the spin filter assembly such that the tube of the spin filter assembly is now under the container closure thereby transferring the suspension from the container closure to the tube of the spin filter assembly; and,
   d) centrifuging the spin filter assembly to separate the desired matrix bound compound of step a from other compounds in solution.

16. The method of using the spin filter assembly of claim 15 further comprising the steps of crosslinking, stopping the crosslinking and washing of the matrix bound compound after step a).

17. The method of using the spin filter assembly of claim 15 wherein the binding of the desired compound in solution with the solid binding matrix of step a) is done in the tube of the spin filter assembly instead of the container closure and it is the container closure that is attached to the open end of the tube in step b).

18. A method of using a spin filter assembly comprising a tube having an open top end, a bottom end opposite the open top end, a body of a first length, an inner diameter, a first outer diameter and a filter means at the bottom end, the tube insertable into an upper portion of a centrifuge holder having a closed lower end, an open upper end, a length longer than the first length of the tube, and a second inner diameter greater than the first outer diameter of the tube; and, a container closure means having an inner diameter, an outer diameter, an open end and a closed end, the open end fitting on top of the open end of the tube in a manner aligning the inner diameter of the container closure with the inner diameter of the tube, the container closure means adapted to hold a desired volume of solution, to reduce the time and process steps for isolating and determining a desired compound in a solution, comprising the steps of:

a) solubilizing a desired compound with a solubilizing solution resulting into a solution containing the desired compound;

b) removing contaminating matters from the solution containing the desired compound by centrifugation and transferring the solution containing the desired compound without the contaminating matter into the container closure of the spin filter assembly;

c) adding a solid binding matrix having a binder reactive to the desired compound to the container closure thereby binding the desired compound in solution resulting into a suspension containing a desired matrix bound compound;

d) attaching the tube of the spin filter assembly on top of the container closure by aligning the open top end of the tube with the open end of the container closure;

e) inverting the spin filter assembly such that the tube of the spin filter assembly is now under the container closure thereby transferring the suspension from the container closure to the tube of the spin filter assembly;

f) separating the desired matrix bound compound from the suspension by centrifuging the spin filter assembly which retains the desired matrix bound compound inside the tube of the spin filter assembly;

g) eluting a desired compound from the desired matrix bound compound isolated from step f with an elution solution introduced into the tube of the spin filter assembly containing the desired matrix bound compound; and, h) analyzing the eluted desired compound in solution.

19. The method of claim 18 wherein the desired compound is a protein.

20. The method of claim 19 wherein the binder is another compound reactive to the protein.

21. The method of claim 19 wherein the solubilizing solution is a buffer containing protease inhibitor and chaotropic salts or protease inhibitor and detergents.

22. The method of claim 19 wherein removing the contaminating matters is done by centrifugation and reaction of the protein with a suspension of solid Protein A/G binding matrix and preimmune serum.

23. The method of claim 19 wherein the solid binding matrix having a binder is Protein A/G with antibodies bound to its surface.

24. The method of claim 19 wherein the protein is first reacted with an antibody before binding to the suspension of the solid binding matrix.

25. The method of claim 24 wherein the solid binding matrix is Protein A/G without antibodies bound to its surface.

26. The method of claim 19 wherein the protein eluting buffer is a Tris solution of sodium dodecyl sulfate, glycerol, mercaptoethanol, and bromophenol blue at pH 6.8.

27. The method of claim 19 wherein the protein eluting buffer is a non-denaturing reagent.

28. The method of claim 27 wherein the non-denaturing reagent is a solution containing polypeptides having the same sequence as the epitope sequence of the protein.

29. The method of claim 18 further comprising the step of chemically crosslinking a binder to a solid matrix before step c).

30. A spin filter assembly, comprising:

a tube having an open top end, a bottom end opposite the open top end, a body of a first length, an inner diameter, a first outer diameter, the tube insertable into an upper portion of a centrifuge holder having a closed lower end, an open upper end, a length longer than the first length of the tube, and a second inner diameter greater than the first outer diameter of the tube;

a flat sintered porous low binding filter frit disc at the bottom end of the tube having a thickness of 0.03–0.04 inches and an air flow rate of 818–2250 ml/min when tested at a set inlet pressure of 1.2 inches of water through an area of 0.75 inches of a one inch sample disc, the filter disc made of a material selected from the group consisting of polyethylene, polypropylene and combinations of polyethylene and polypropylene; and, a container closure means having an inner diameter, an outer diameter, an open end and a closed end, the open end fitting on top of the open end of the tube in a manner aligning the inner diameter of the container closure with the inner diameter of the tube, the container closure means adapted to hold a desired volume of solution.

31. The spin filter assembly of claim 30 wherein the filter frit disc is made of a porous ultrahigh molecular weight polyethylene material.

32. The spin filter assembly of claim 30 wherein the spin filter assembly is made of a plastic material.

* * * * *